United States Patent
Carey

(10) Patent No.: US 6,551,783 B1
(45) Date of Patent: Apr. 22, 2003

(54) QUANTITATIVE ANALYSIS OF GENE EXPRESSION USING PCR

(75) Inventor: Janet E. Carey, Herts (GB)

(73) Assignee: Pharmagene Laboratories Limited, Royston (GB)

( * ) Notice: Subject to any disclaimer, the term of this patent is extended or adjusted under 35 U.S.C. 154(b) by 0 days.

(21) Appl. No.: 09/744,154

(22) PCT Filed: Jul. 21, 1999

(86) PCT No.: PCT/GB99/02359

§ 371 (c)(1),
(2), (4) Date: Feb. 1, 2001

(87) PCT Pub. No.: WO00/05409

PCT Pub. Date: Feb. 3, 2000

(30) Foreign Application Priority Data

Jul. 21, 1998 (GB) ............................................. 9815799

(51) Int. Cl.[7] ........................... C12Q 1/60; C12P 19/34; C07H 21/04
(52) U.S. Cl. ......................... 435/6; 435/91.1; 435/91.2; 536/24.31; 536/24.32; 536/24.33
(58) Field of Search ........................ 435/6, 91.1, 91.2; 536/24.31, 24.32, 24.33

(56) References Cited

FOREIGN PATENT DOCUMENTS

| EP | 0 639 647 | 2/1995 |
| EP | 0 713 921 | 5/1996 |
| WO | WO 94 23023 | 10/1994 |
| WO | WO 97 29210 | 8/1997 |
| WO | WO 97 46714 | 12/1997 |

OTHER PUBLICATIONS

Marmaro, J., "A TaqMan Multiplex PCR mRNA Quantitation Assay", Clin. Chemistry, vol. 41, p. 1685 (1995).*
Woudenberg et al, "Quantitative PCR by Real Time Detection", Proceedings of the SPIE, vol. 2680, pp. 306–315.
Heid et al, "Real Time Quantitative PCT", Genome Research, 1996, pp. 986–994.

* cited by examiner

*Primary Examiner*—Kenneth R. Horlick
*Assistant Examiner*—Teresa Strzelecka

(57) ABSTRACT

The invention provides an improved method for quantitation of two target genes in a simultaneous PCR, without the need to determine limiting primer concentrations for both targets. In particular, the invention provides a method of quantitation of expression of a first and a second target protein-encoding nucleic acids using a PCR based assay in which amplification of nucleic acid is detected by release of a reporter fluorescent signal which is measured as a nomialized reporter value ("deltaRn").

6 Claims, No Drawings

QUANTITATIVE ANALYSIS OF GENE EXPRESSION USING PCR

FIELD OF THE INVENTION

The present invention relates to a method of quantitative analysis of gene expression that is particularly suited for use in automated assay systems involving fluorescent dyes.

BACKGROUND TO THE INVENTION

Of the systems currently available for automated assay to determine mRNA copy number of target gene transcripts the Perkin Elmer Applied Biosystems® ABI PRISM® 7700 sequence detection system and associated TaqMan® probes are one of the most efficient and effective and most widely used.

The Perkin Elmer System is a PCR (Polymerase Chain Reaction) based system in which a probe labelled with a fluorescent reporter molecule (typically 6-FAM, JOE or VIC—see below) and a quencher dye (e.g. TAMRA—see below) is provided which hybridises to the target nucleic acid between the site of hybridisation of the forward and reverse PCR primers. While intact, any fluorescence emitted from the probe's reporter molecule is absorbed by the quencher.

During the primer extension phase of the PCR, the Taq polymerase displaces the reporter probe from the strand of DNA being amplified, and in doing so the 5'>3' exonuclease activity inherent in the polymerase cleaves the probe, separating the reporter molecule from the vicinity of the quencher. The increase in fluorescent reporter signal within a reaction is a direct measure of the accumulation of PCR product.

The ABI 7700 has a built in thermal cycler and a laser directed at each sample well in which PCR is performed via bi-directional fibre optic cables. Emitted fluorescence travels through the cables to a detector, where signals from released reporter molecules which fall between 520 and 66 nM are collected every few seconds. The increase in fluorescent reporter signal within a reaction is a direct measure of the accumulation of PCR product. The output of the assay is measured as a normalised reporter value, ΔRn. The normalised reporter value for any sample is calculated by the ABI 7700 sequence detection software by dividing the reporter fluorescent signal by the signal from a reference reporter (ROX) incorporated in the reaction and deducting a baseline fluorescence signal which is established during the first few cycles of PCR. The ΔRn values are plotted against thermal cycle number to allow visualisation of the extent of PCR product generation. The starting copy number of a target sequence (Cn) is established by determining the fractional cycle number (Ct) at which a PCR product is first detected— the point at which the fluorescence signal passes above a threshold baseline.

To determine Ct the Sequence Detection application collects data from the first few PCR cycles and calculates the average Rn and the standard deviation of the Rn by a default factor of 10 to define a threshold. Finally, the algorithm searches the data for a point that exceeds the baseline by the value of the threshold. The cycle at which this point occurs is defined as Ct. Ct represents a detection threshold for the Sequence Detector. Ct is dependent on the starting template copy number, and the efficiency of both the DNA amplification the PCR system and the cleavage of the fluorogenic probe. When the starting concentration of a template remains constant as the concentration of other PCR components varies, the most efficient PCR system has the lowest Ct.

Quantification of target is established through comparison of experimental Ct values with a standard curve.

The conventional use of the Perkin Elmer TaqMan® assay system had been limited to the use of single dye probes. However, in recent times the system has been adapted for use of multiple reporter dyes within a single reaction tube to perform a convenient multiplex assay in which the mRNA copy number for more than one target gene transcript can be determined within a single tube. To achieve this there must be more than one primer pair present in the tube which presents a problem if there are differences in the initial copy numbers of the gene sequences to be expressed. The more common gene sequence may well exhaust the reagents within the tube preventing amplification of the less common sequence(s).

Perkin Elmer have sought to overcome this problem by limiting the production of the assay PCR products derived from each of the two or more target or marker gene sequences to ensure that if one of the sequences is more abundant than another there will nonetheless be sufficient reagents remaining in the reaction mix to amplify the less abundant even if its amplification and hence detection does not start until the reaction involving the more abundant transcript has run to completion.

In their instructions on how to implement their multiplexing method, Perkin Elmer advise the user (user Bulletin #2 ABI PRISM 7700 Sequence Detection System of Dec. 11, 1997) that if the user does not know the relative abundance of each RNA to be assayed for, then limiting primer concentrations will need to be defined for each by running a matrix of forward and reverse primer concentrations for each and identifying the concentrations as those that show a reduction in ΔRn but little effect on Ct (threshold cycle). Such characterisation of limiting primer concentrations is inherently time consuming. However, the only alternative proposed by Perkin Elmer is to use rRNA as one of the target gene transcripts avoiding the need for determining limiting primer concentration based upon the fact that rRNA is known to be extremely abundant and will therefore inevitably be more abundant than the other chosen target mRNA in the assay.

It is one general objective of the present invention to provide a method of multiplexing that avoids the need for characterisation of the limiting primer conditions for each of the gene targets without being restricted to use of rRNA as one of the targets.

SUMMARY OF THE INVENTION

According to the present invention there is provided a method of quantitative analysis of gene expression utilising a respective fluorescent reporter signal for at least a first and a second target gene within a single replication reaction vessel the method comprising:

(i) determining a suitable restricted concentration of primer for replication of the first target gene, wherein the concentration of primer is selected to provide a robust, but limited fluorescent amplification signal; and (ii) determining a suitable concentration of primer for replication of the second target gene, wherein the concentration of primers is selected to give the most efficient detection of amplification as measured by accumulation of fluorescent signal; and (iii) utilising the selected primer concentration, determining a suitable concentration of second target gene probe, wherein the concentration of the second target gene probe is selected to provide a fluorescent signal that is at least four times greater than the fluorescent signal of the selected first gene primer concentration.

Suitably the concentration of primer is, in each case, determined for both forwards and reverse primers. As used in step (i) of the method the term "limited" means not maximal and the term robust means strong and readily recognisable.

Preferably in step (ii) the concentration of primer(s) is selected to give the earliest detection of amplification.

Suitably the first gene primer concentrations correspond to ΔRn of less than 0.3 and preferably the selected target gene probe concentration corresponds to a target fluorescent signal ΔRn of between 1.5 and 6.

In a more particular aspect, the invention provides a method of quantitation of expression of a first and a second target protein-encoding nucleic acids using a PCR based assay in which amplification of nucleic acid is detected by release of a reporter fluorescent signal which is measured as a normalised reporter value ("ΔRn"), the method comprising:

providing a limiting concentration of a first primer pair, the first primer pair being adapted for amplification of a desired first target, the limiting concentration being selected to provide a relatively low ΔRn value as measured by release of a first fluorescent reporter compound from a first reporter probe;

selecting a non-limiting concentration of a second primer pair and probe set, the second primer pair being adapted for amplification of a desired second target, the amplification being measured by release of a second fluorescent reporter compound from a second reporter probe, the concentration being selected to provide a ΔRn value of from three to forty times that provided by said first reporter compound;

bringing said first and second primer pairs and probes at their limited and selected concentrations respectively into contact with a sample of nucleic acid;

performing a polymerase chain reaction under conditions in which the release of the first and second reporter compounds is measured; and quantitating the amount of first and second target nucleic acids.

DESCRIPTION OF PREFERRED EMBODIMENT

The general protocol of the method embodying the present invention will now be outlined and then supported by experimental examples.

As indicated above, the invention provides an efficient and time-saving solution for the measurement of two different target nucleic acids in a single sample, without being limited to either selecting rRNA as one of the samples or needing to determine limiting primer concentrations for both targets. In this way, two different protein-encoding nucleic acid targets, particularly mRNA (optionally in the form of cDNA) (although genomic DNA may also be measured).

In measuring mRNA, a particularly preferred limited reporter probe is one which spans two exon sequences in such a manner that it does not hybridise to either of the two exons individually under PCR conditions but is capable of hybridising to the sequences when brought together in mRNA (for example the probe could be 24 nucleic acids in size representing 12 nucleic acids of the 3' end of the first exon and 12 of the 5' end of the second exon). This provides a level of additional control to ensure the amplified product detected is from a good quality mRNA preparation. Thus the invention may be used to provide quantitation of two nucleic acid targets from genes which are transcribed into polyA$^+$ RNA, spliced and translated.

In one embodiment, the first target may be a marker gene such as a ubiquitously expressed marker gene. Some of these genes may sometimes show little or no variation in expression between tissues, and may be used as a means of normalising different samples for loading of starting material whilst measuring the abundance of a second target within them.

Examples of such marker genes include genes involved in basic biosynthetic and metabolic pathways, for example glyceraldehyde-3-phosphate dehydrogenase, alpha actin, heat shock protein 90a, DAD-1 (Defender Against Cell Death 1) and collagen 3.

Alternatively the first target nucleic acid, as well as the second target nucleic acid, may be transcripts of genes whose expression level varies between different samples, such as different tissue types from the human or animal body. Such targets include oncogenes (e.g. myc, ras, erb, and the like), receptors (e.g. TNF-α, interferon and interleukin subtype receptors), cytokines (e.g. TNF-α, interferons, interleukins, and the like), growth factors (EGF, PDGF, VEGF, etc), or members of the immunoglobulin superfamily (including T-cell receptors and HLA genes). Targets may also include uncharacterised or partially characterised EST sequences, e.g. EST sequences which include particular domains of interest.

The flanking PCR primer concentrations of the first (e.g. marker) nucleic acid target can be determined in a single experiment by combining a range of forward primer concentrations, typically 10–50 nM with an equivalent range of reverse primer concentrations in the presence of an excess concentration of probe (100 nM). The concentrations of primers selected should provide a robust, but limited fluorescent amplification signal, typically with a ΔRn of less than 0.5, preferably less than 0.3, as determined in relation to the ROX baseline presently used in the ABI 7700 system used in the art. This determination will provide a limiting concentration of primers for the first primer pair. The limiting concentration is defined by the ABI User Bulletin #2 as that providing a reduction in the ΔRn value (compared to that which provides for exhaustion of reagents before primers) but which has little effect on the threshold Ct. In practice, the aim is to determine a concentration such that the ΔRn value is lowered to, or just above, the value at which the Ct starts to increase when the primer concentrations are lowered further. When measured against the normalised reporter ROX, the ΔRn for the limiting primer concentration is preferably less than 0.5, more preferably less than 0.3.

It is important that the fluorescent signal generated in this reaction is limited for two reasons. Firstly, the emission spectra of the two dyes currently most often employed in the reporter probes (e.g. selected from 6-FAM and VIC or JOE) overlap. If a large amount of fluorescence is generated from the first target nucleic acid it can contribute to the signal generated from the second reporter probe fluorophore causing that signal to apparently start to accumulate early and therefore give an inaccurate determination of second target abundance. Secondly, the limited generation of a fluorescent signal (where the fluorescent probe is not the limiting reagent) reflects limited production of first target amplicon, this preserves reagents for amplification of the target of interest.

It is not essential that the determination of the limiting concentration is performed each time a second target gene is quantified.

It is also a feature of the invention that unlike the protocol of the prior art, it is not necessary to make a determination of a limiting concentration of the primers and probe set for the second target gene. Instead, we have been able to define a simple and robust set of conditions which, if met, will result in an accurate dual quantitation of two target nucleic acids in a single sample. These conditions are in part a measure of the efficiency of amplification of the second primer and probe set, such that when replicated in a reaction with a limiting concentration of a first primer and probe set, will allow for both target genes to be quantified, irrespective of their relative abundance.

In a typical selection, we provide a known number of copies of a target nucleic acid together with primer and probe concentrations which are non-limiting in the sense that they could be lowered further without significantly altering the Ct.

Typically, we provide about 10,000 copies of a target nucleic acid (optionally in the form of genomic DNA (provided the probe is not exon-spanning)) and at least 250 nM of each of the forward and reverse primers (e.g. from 250 to 500 nM, e.g. about 250–350 nM, most preferably about 300 nM, the concentrations of forward and reverse primers being independently selected but desirably the same), and at least 100 nM of primer probe, (e.g. from 100 to 300 nM, preferably about 150 to 250 nM, e.g. about 200 nM). The term "about" indicates a margin of error of ±10%.

A PCR is performed in which amplification of the nucleic acid is detected by release of a reporter fluorescent signal which is measured as a normalised reporter value ("ΔRn") by reference to the reporter dye ROX. Where the ΔRn is found to be from 1.5 to 6.0 and the Ct is found to be between 24 and 26, then the primer and probe set may be used at the selected concentrations without any need for determination of a limiting concentration. Should the ΔRn and Ct values fall outside the target range, the probe and/or primer concentrations may be adjusted as required in order to achieve the target range.

This range of ΔRn values will thus be from 3 to 40 times the preferred range of ΔRn values for the first target nucleic acid. More preferably, the range is from 4 to 40, even more preferably from 4 to 30 and most preferably from 4 to 20 times.

The conditions here are of course relative to the copy number of the target nucleic acid, and may be adjusted by those of skill in the art to allow for greater or lower copy numbers of second target, with a consequential adjustment in the acceptable Ct.

Once the second primer pair concentration has been selected, the dual quantitation of the first and second target may be performed. The reaction will use standard PCR conditions, and be run typically for 30–40 cycles. Suitable conditions may be provided with a variety of commercially available PCR kits, including those designed for use with commercial PCR apparatus, such as the ABI Prism 7700. The conditions set out in the accompanying examples may be used. The concentrations of both deoxynucleotides and polymerase (e.g. AmpliTaq®) enzyme must be sufficient to support amplification of two targets.

The method of the present invention may be used across multiple RNA samples derived from different tissues to generate maps of transcript expression or to profile the expression of many different transcripts in the same RNA sample.

In quantitating the amount of first and second target nucleic acids, this may be by determination of copy number, calculated by reference to the Ct value (this can be performed by the software provided for use with PCR detection apparatus) or may be a relative quantitation, e.g. the ratio of targets in the sample or between different samples (e.g. different tissue types of the human or animal body).

The fluorescent reporter dyes may be any dye which can be attached to a reporter nucleic acid probe and which has a suitable λmax for detection in a PCR apparatus, generally between 500 and 660 nm. Commercially available dyes include:

6-FAM (6-carboxy-fluorescein);
JOE (2,7-dimethoxy-4,5-dichloro-6-carboxy-fluorescein);
ROX (carboxy-X-rhodamine);
TET (tetrachloro-6-carboxy-fluorescein); and
VIC (proprietary to and available from Perkin Elmer).

In the invention, it is desirable to use two dyes which have a large difference in emission maxima, such as 6-FAM (λmax 518 nm) and JOE (λmax 554) or 6-FAM and VIC (λmax 550 nm)

The reporter dyes are quenched by a suitable quencher, of which many exist, including a variety of rhodamine dyes. A suitable dye is TAMRA (6-carboxy-tetramethyl-rhodamine).

The normalised reporter value may be determined against a dye with a λmax above the values of the reporter dyes. A currently preferred reference dye is ROX, against which the values described herein have been normalised. Where a different reference dye is used, the values given herein may be adjusted by recalculation by reference to the difference in values of ROX and the other reference.

In summary, the only previously described Taqman® assay incorporating two targets in a single tube requires optimisation of reaction conditions for both marker and target genes for every assay configured unless rRNA is used as the marker gene. The system described here allows a single determination of marker gene conditions which can then be used universally with any target optimised to run in conjunction with it. The system offers a significant advantage over that previously described by allowing choice of marker gene transcript, reducing assay development time and therefore increasing throughput for researchers characterising multiple gene targets. Furthermore the method of the present invention in contrast to the prior art economises on use of the expensive primers, thereby providing valuable cost economy in the execution of the assay.

The present invention is illustrated by the following examples.

EXAMPLE 1

Primer/probe Design

A pair of primers and a TaqMan® probes were designed to amplify a specific sequence from a human seven transmembrane receptor (GenBank accession number L24470)

Primer 1: 5'AAGGATCTAAGATTTGATTCCATGTTG3' SEQ ID NO:1
Primer 3: 5'GAATAAATGGAAATCATTCTCTG-GAAAC3' SEQ ID NO:2
Probe 5: 5'TGTGAAACAACACTTTTTGCTCTC-CGAATG3' SEQ ID NO:3

In addition a pair of primers and a TaqMan® probe were designed which cross an intron/exon boundary and amplify a portion of the human GAPDH gene Primer 2: 5'CAGAGTTAAAAGCAGCCCTGGT3' SEQ ID NO:4
Primer 4: 5'GAAGGTGAAGGTCGGAGTCAAC3' SEQ ID NO:5

Probe 6: 5'TTTGGTCCGTATTGGGCGCCT3' SEQ ID NO:6

Probe 5 is labelled with the fluor 6-FAM while probe 6 is labelled with the fluor JOE.

DNase Treatment of Total RNA

For each tissue tested 2.2 µg of total RNA was digested with 2 units of Rnase free Dnase (Gibco BRL) for 15 minutes at room temperature in a 20 µl volume of 1× Dnase buffer (Gibco BRL). The reaction was stopped by addition of 2 µl of 25 mM EDTA solution. The samples were then incubated at 65° C. for 10 minutes to inactivate the enzyme.

First Strand cDNA Synthesis

For each tissue tested 100 ng of total RNA was used as template for first strand cDNA synthesis. The RNA in a volume of 4 µl and in the presence of 50 nM primers 1 and 2, 1×PCR buffer II (Perkin Elmer) and 5 mM $MgCl_2$ was heated to 72° C. for 5 minutes and cooled slowly to 55° C. After addition of all other reagents, the 6 µl reaction was incubated at 48° C. for 30 minutes followed by an enzyme inactivation step of 90° C. for 5 minutes. The final reaction conditions were as follows: 1×PCR buffer II, 5 mM $MgCl_2$, 1 mM dATP, dUTP, dGTP, dCTP, 12.5 units MuLV reverse transcriptase (Gibco BRL). By increasing the scale of the reaction it is possible to prime for up to six targets in one reverse transcription.

PCR Amplification of First Strand cDNA Products

The cDNA derived from 100 ng total RNA for each sample was subjected to PCR amplification in a single reaction to identify both target and GAPDH transcripts. The final primer/probe concentrations for target were 300 nM primer 1, 300 nM primer 3 and 150 nM probe 5, those for GAPDH were 20 nM primer 2, 20 nM primer 4 and 100 nM probe 6. The final concentration of other reagents in the reaction were 4.5% glycerol, 1×1 TaqMan® buffer A (Perkin Elmer), 6.25 mM $MgCl_2$, 430 µM dATP, dUTP, dGTP, dCTP, 2.5 units AmpliTaq® Gold. The PCR amplification was carried out in the ABI 7700 sequence detection system, an initial enzyme activation step of 94° C. for 12 min was followed by 45 cycles of 94° C. 15 secs, 60° C. 1 min (minimum ramp time) For comparative purposes cDNA derived from 100 ng cDNA was subjected to PCR amplification in a reaction containing only the primer/probe set for target and run in previously optimised assay conditions of 5% glycerol, 6.5 mM $MgCl_2$, 300 µM dATP, dUTP, dGTP, dCTP, 1.25 units AmpliTaq® Gold.

Results

The results for five different RNA samples are illustrated in Table 1 and compare both the threshold cycle for the detection of FAM fluorescent signal (Ct) and the log of the starting copy (log Cn) number for the target transcript in the single and dual probe reactions. The correlation coefficient for both groups of data is greater than 0.9 showing that there is almost absolute proportionality in detection of target between the two data sets and that the presence of an additional fluorescent probe in the reaction does not significantly affect the accuracy of specific sequence detection. The threshold cycle for detection of JOE fluorescent signal for GAPDH is shown in table 2 and can either be used as a marker for the presence of intact RNA or as a means of normalisation in an appropriate experimental set up. The average ΔRn in the experimental run for the target primer/probe set is 3.19 and that for the marker gene 0.15.

TABLE 1

| Tissue | Dual probe Ct (6-FAM) | Single probe Ct (6-FAM) | Dual probe Log Cn | Single probe Log Cn |
|---|---|---|---|---|
| uterus endometrium | 33.27 | 33.11 | 2.27 | 2.30 |
| liver | 27.28 | 27.34 | 3.60 | 3.59 |
| gall bladder | 27.48 | 27.58 | 3.55 | 3.53 |
| stomach fundus mucosa | 28.10 | 27.88 | 3.41 | 3.46 |
| ileum mucosa | 32.69 | 32.41 | 2.39 | 2.46 |

TABLE 2

| Tissue | Dual probe Ct (JOE) |
|---|---|
| uterus endometrium | 21.48 |
| liver | 21.16 |
| gall bladder | 21.14 |
| stomach fundus mucosa | 23.36 |
| ileum mucosa | 24.2 |

EXAMPLE 2

Primer Probe Design

A pair of primers and TaqMan® probes were designed to amplify a specific sequence from a human seven transmembrane receptor (GenBank accession number U19487)

Primer 7: 5'TCCGCAGCGGCTTCTC3' SEQ ID NO:7

Primer 8: 5'GCCTGCAACTTCAGTGTCATTC3' SEQ ID NO:8

Probe 9: 5'CATCCGCATGCACCGCCG3' SEQ ID NO:9

These were used in conjunction with the GAPDH primer/probe set described in Example 1.

Probe 9 is labelled with the fluor 6-FAM while probe 6 is labelled with the fluor JOE.

DNase Treatment of Total RNA

For each tissue tested 2.2 µg of total RNA was digested with 2 units of Rnase free Dnase (Gibco BRL) for 15 minutes at room temperature in a 20 µl volume of 1×Dnase buffer (Gibco BRL). The reaction was stopped by addition of 2 µL of 25 mM EDTA solution. The samples were then incubated at 65° C. for 10 minutes to inactive the enzyme.

First Strand cDNA Synthesis

For each tissue tested 10 ng was used as template for first strand cDNA synthesis. The RNA in a volume of 4 µl and in the presence of 50 nM primers 7 and 2, 1×PCR buffer II (Perkin Elmer) and 5 mM $MgCl_2$ was heated to 72° C. for 5 minutes and cooled slowly to 55° C. After addition of all other reagents, the 6 µl reaction was incubated at 48° C. for 30 minutes followed by an enzyme inactivation step of 90° C. for 5 minutes. The final reaction conditions were as follows: 1×PCR buffer II, 5 mM $MgCl_2$, 1 mM dATP, dUTP, dGTP, dCTP, 12.5 units MuLV reverse transcriptase (Gibco BRL). As with Example 1, it is possible, by increasing the scale of the reaction, to prime for up to six targets in one reverse transcription.

PCR Amplification of First Strand cDNA Products

The cDNA derived from 100 ng total RNA for each sample was subjected to PCR amplification in a single reaction to identify both target and GAPDH transcripts. The final primer/probe concentrations for target were 300 nM primer 7, 300 nM primer 8 and 150 nM probe 9 (these concentrations gave an Rn of 4.8 in the optimisation protocol), those for GAPDH were 20 nM primer 2, 20 nM primer 4 and 100 nM probe 6. The final concentration of other reagents in the reaction were 4.5% glycerol, 1×TaqMan® buffer A (Perkin Elmer), 6.24 mM MgCl$_2$, 430 µM dATP, dUTP, dGTP, dCTP, 2.5 units AmpliTaq® Gold. The PCR amplification was carried out in the ABI 7700 sequence detection system, an initial enzyme activation step of 94° C. for 12 min was followed by 45 cycles of 94° C. 15 secs, 60° C. 1 min (minimum ramp time). For comparative purposes cDNA derived from 100 ng cDNA was subjected to PCR amplification in a reaction containing only the primer/probe set for target and run in previously optimised assay conditions of 5% glycerol, 6.5 mM MgCl$_2$, 300 µM, dATP, dUTP, dGTP, dCTP, 1.25 units AmpliTaq® Gold.

Results

The results of five different RNA samples are illustrated in Table 3 and compare both the threshold cycle for the detection of 6-FAM fluorescent signal (Ct) and the log of the starting copy (log Cn) number for the target transcript in the single and dual probe reactions. The correlation coefficient for both groups of data is greater than 0.9 showing that there is almost absolute proportionality in detection of target between the two data sets and that the presence of an additional fluorescent probe in the reaction does not significantly affect the accuracy of specific sequence detection. The threshold cycle for detection of JOE fluorescent signal for GAPDH is shown in Table 4 and can either be used as a marker for the presence of intact RNA or as a means of normalisation in an appropriate experimental set up. The average ΔRn in the experimental run for the target primer/probe set is 3.85, that for the marker gene 0.14.

TABLE 3

| Tissue | Dual probe Ct (6-FAM) | Single probe Ct (6-FAM) | Dual probe Log Cn | Single probe Log Cn |
| --- | --- | --- | --- | --- |
| uterus endometrium | 30.3 | 30.5 | 2.81 | 2.77 |
| liver | 30.39 | 30.03 | 2.81 | 2.89 |
| gall bladder | 29.3 | 29.44 | 3.07 | 3.04 |
| stomach fundus mucosa | 30.1 | 29.4 | 2.88 | 3.04 |
| ileum mucosa | 32.4 | 32.06 | 2.34 | 2.41 |

TABLE 4

| Tissue | Dual probe Ct (JOE) |
| --- | --- |
| uterus endometrium | 20.46 |
| liver | 20.06 |
| gall bladder | 20.84 |
| stomach fundus mucosa | 23.02 |
| ileum mucosa | 23.26 |

EXAMPLE 3

Pairs of primers and TaqMan® probes were designed to amplify specific sequences for the following targets (listed as GenBank accession numbers):

| X52773 | D11131 | U03504 | U87460 |
| --- | --- | --- | --- |
| U66661 | J05556 | M63904 | X15376 |
| X57766 | AF043101 | | |

These were used in conjunction with the GAPDH primer/probe set described in Example 1 to amplify their respective targets from a total RNA sample isolated from human liver. The probes for the targets listed above were all labelled with the fluor 6-FAM while the probe for GAPDH is labelled with JOE.

Selection of Primer/probe Concentrations for the Non Limited Targets

A PCR reaction is performed using the target gene primers and probe at a final concentration of 300 nM forward primer, 300 nM reverse primer and 200 nM probe on 30 ng of human genomic DNA in a 25 µl reaction containing 4.5% glycerol, 1×TaqMan® buffer A (Perkin Elmer) 6.25 mM MgCl$_2$, 430 µM dATP, dUTP, dGTP, dCTP, 2.5 units of AmpliTaq® Gold. The PCR amplification was carried out in the ABI7700 sequence detection system, an initial enzyme activation step of 94° C. for 12 minutes was followed by 40 cycles of 94° C. 15 seconds, 60° C. 1 minute (minimum ramp time). If the reaction fulfils the following criteria, the primer/probe set can be used in conjunction with any primer limited set irrespective of the relative abundance of the two targets.

The Ct falls between 24 and 26 (where the threshold is set at 0.15)

ΔRn at reaction plateau falls between 1.5 and 6

A single reaction product of the predicted size is generated by the PCR reaction as assessed by gel electrophoresis If the ΔRn is >6 or <1.5 the probe concentration can be adjusted without further experimentation to fulfil the reaction parameters by assuming a linear relationship between probe concentration and ΔRn.

Where the ΔRn was outside the above range, the selection protocol was re-run with 50 nM more or less probe so that the ΔRn value was increased or decreased as required to meet the criteria.

The following table shows the Ct and ΔRn values for the non-limiting forward (F) and reverse (R) primer and probe (P) concentrations selected.

| Target | Concentration F/R/P | Ct on 30 ng of human genomic DNA | ΔRn |
| --- | --- | --- | --- |
| X52773 | 300/300/150 | 24.02 | 4 |
| D11131 | 300/300/150 | 24.16 | 6 |
| U87460 | 300/300/250 | 24.03 | 4 |
| U03504 | 300/300/250 | 24.744 | 1.6 |
| U66661 | 300/300/250 | 24.399 | 3.5 |
| J05556 | 300/300/250 | 24.58 | 4 |
| M63904 | 300/300/150 | 24.346 | 4.5 |
| X15376 | 300/300/200 | 24.41 | 3 |
| X57766 | 300/300/250 | 25.855 | 5 |
| AF043101 | 300/300/200 | 24.46 | 3 |

The selected probe-primer set was used in multiplex assay as follows.

DNase Treatment of Total RNA 2.2 µg of total RNA isolated from human liver was digested with 2 units of RNase free DNase (Gibco BRL) for 15 minutes at room temperature in a 20 µl volume of 1×DNase buffer (Gibco BRL). The reaction was stopped by the addition of 2 µl of 25 mM EDTA solution. The samples were then incubated at 65° C. for 10 minutes to inactivate the enzyme.

First Strand cDNA Synthesis

For each transcript to be measured 100 ng of total RNA was used as a template for cDNA synthesis. The RNA in a volume of 4 µl and in the presence of 50 nM reverse primers for target and GAPDH, 1×PCR Buffer II (Perkin Elmer) and 5 mM MgCl$_2$ was heated to 72° C. for 5 minutes and cooled slowly to 55° C. After addition of all other reagents, the 6 µl reaction was incubated at 37° C. for 30 minutes followed by an enzyme inactivation step of 90° C. for 5 minutes. The final reaction conditions were as follows: 1×PCR buffer II, 5 mM MgCl$_2$, 1 mM dATP, dTTP, dGTP, dCTP, 12.5 units MuLV reverse transcriptase (Gibco BRL).

PCR Amplification of First Strand cDNA Products

The cDNA derived from 100 ng total RNA from human liver was subjected to PCR amplification in a single reaction to identify both target and GAPDH transcripts. The final primer/probe concentrations for target were as shown in the table above, those for GAPDH were 20 nM primer 2, 20 nM primer 4 and 100 nM probe 6. The final concentration of other reagents in the reaction were 4% glycerol, 0.66× TaqMan® buffer A (Perkin Elmer), 6 mM MgCl$_2$, 358 μM dATP, dUTP, dGTP, dCTP, 2.5 units AmpliTaq® Gold. The PCR amplification was carried out in the ABI 7700 sequence detection system, an initial enzyme activation step of 94° C. for 12 min was followed by 45 cycles of 94° C. 15 secs, 60° C. 1 min (minimum ramp time).

Results

The results for the detection of the eleven targets each in 100 ng total RNA isolated from human liver are illustrated in the following table and show both the threshold cycle for the detection of 6-FAM and JOE fluorescent signals (6-FAM Ct and JOE Ct) and the starting copy number (Cn) for both the GAPDH and target transcripts in each reaction. The standard error of the mean for the GAPDH Ct values is 0.011621 showing that the reaction proceeds with the same efficiency irrespective of the abundance of the second target.

| Target | 6-FAM Ct | 6-FAM Cn | JOE Ct | JOE Cn |
|---|---|---|---|---|
| X52773 | 21.76 | 108,751 | 22.04 | 91,023 |
| D11131 | 23.61 | 33,559 | 21.97 | 95,164 |
| U87460 | 26.04 | 7,163 | 22.07 | 89,304 |
| U03504 | 28.95 | 1,127 | 22.07 | 89,304 |
| U66661 | 29.96 | 593 | 22.03 | 91,803 |
| J05556 | 31.68 | 199 | 22.02 | 92,187 |
| M63904 | 32.52 | 117 | 22.12 | 86,510 |
| X15376 | 36.8 | 8 | 22.04 | 91,023 |
| X57766 | 37.09 | 6 | 22.07 | 89,304 |
| AF043101 | 39.52 | 1 | 22.06 | 89,873 |

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity and understanding, it will be readily apparent to those of skill in the art that certain changes and modifications may be made thereto without departing from the spirit or scope of the appended claims.

What is claimed is:

1. A method of quantitation of expression of a first and a second target protein-encoding nucleic acids using a PCR based assay in which amplification of nucleic acid is detected by release of a reporter fluorescent signal which is measured as a normalised reporter value ("ΔRn"), the method comprising:

providing a limiting concentration of a first primer pair, the first primer pair being adapted for amplification of a desired first target, the limiting concentration being selected to provide a first ΔRn value as measured by release of a first fluorescent reporter compound from a first reporter probe;

selecting a non-limiting concentration of a second primer pair and probe set, the second primer pair being adapted for amplification of a desired second target, the amplification being measured by release of a second fluorescent reporter compound from a second reporter probe, the concentration being selected to provide a second ΔRn value of from three to forty times that provided by said first reporter compound;

bringing together said first and second primer pairs and probes at their limited and selected concentrations respectively into contact with a sample of nucleic acid;

performing a polymerase chain reaction under conditions in which the release of the first and second reporter compounds is measured; and quantitating the amount of first and second target nucleic acids.

2. A method according to claim 1 wherein said normalised reporter value is normalised by reference to the reporter dye ROX, and said first ΔRn value is less than 0.5.

3. A method according to claim 2 wherein the ΔRn of said second reporter compound is from 1.5 to 6.0.

4. A method according to claim 1 wherein said selecting is by a process which comprises:

providing about 10,000 copies of said second target nucleic acid;

providing primer concentrations in excess of 250 nM and a probe concentration in excess of 100 nM;

performing an amplification reaction in which amplification of nucleic acid is detected by release of a reporter fluorescent signal which is measured as a normalised reporter value ("ΔRn"), selecting the primer and probe concentrations used as a non-limiting concentration when the fractional cycle number at which amplification of a second target sequence is detected is from 24 to 26 and the reporter value is normalised by reference to the reporter dye ROX is from 1.5 to 6.0.

5. A method according to claim 1 wherein said first desired target is a ubiquitously expressed marker gene.

6. A method according to claim 5 wherein said marker gene is GAPDH (glyceraldehyde-3-phosphate dehydrogenase).

* * * * *

SEQUENCE LISTING

<160> NUMBER OF SEQ ID NOS: 9

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1
aaggatctaa gatttgattc catgttg                                       27

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 2
gaataaatgg aaatcattct ctggaaac                                      28

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
tgtgaaacaa cactttttgc tctccgaatg                                    30

<210> SEQ ID NO 4
<211> LENGTH: 22
<212> TYPE: DNA
<213> ORGANISM: Artificial Sequence -continued

```
<220> FEATURE:
<223> OTHER INFORMATION: Description of Artificial Sequence: Primer

<400> SEQUENCE: 4
cagagttaaa agcagccctg gt                                               22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 5
gaaggtgaag gtcggagtca ac                                               22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
tttggtccgt attgggcgcc t                                                21

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 7
tccgcagcgg cttctc                                                      16

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
gcctgcaact tcagtgtcat tc                                               22

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
catccgcatg caccgccg                                                    18
```